United States Patent [19]

Enhorning

[11] Patent Number: 5,007,894
[45] Date of Patent: Apr. 16, 1991

[54] FEMALE INCONTINENCE DEVICE

[76] Inventor: Goran Enhorning, 21 Oakland Pl., Buffalo, N.Y. 14222

[21] Appl. No.: 309,383

[22] Filed: Feb. 10, 1989

[51] Int. Cl.$^5$ .............................................. A61F 2/00
[52] U.S. Cl. ..................................... 600/29; 600/31; 128/DIG. 25
[58] Field of Search ..................... 600/29–31; 128/DIG. 25, 897–899, 79; 623/11, 12

[56] References Cited

U.S. PATENT DOCUMENTS

| | | |
|---|---|---|
| 2,494,393 | 1/1950 | Lamson . |
| 2,638,093 | 12/1959 | Kulick ........................ 120/DIG. 25 |
| 3,066,667 | 10/1960 | Berry ...................... 600/30 |
| 3,080,865 | 3/1963 | Vincent . |
| 3,554,184 | 1/1971 | Habib . |
| 3,646,929 | 3/1972 | Bonnar . |
| 3,705,575 | 12/1972 | Edwards . |
| 3,866,611 | 2/1975 | Baumrucker . |
| 4,019,498 | 4/1977 | Hautrey et al. ........................ 600/29 |
| 4,139,006 | 2/1979 | Corey . |
| 4,290,420 | 9/1981 | Manetta . |
| 4,428,365 | 1/1984 | Hakky . |
| 4,785,828 | 11/1988 | Maurer ................................ 128/788 |

OTHER PUBLICATIONS

Goran Enhorning; "Simultaneous Recording of Intra-vesical and Intra-Urethral Pressure", *Acta Chirurgica Scandinavica*, Supplementum 275, Stockholm, 1961.

Primary Examiner—C. Fred Rosenbaum
Assistant Examiner—Kathleen Daley
Attorney, Agent, or Firm—Hodgson Russ Andrews Woods & Goodyear

[57] ABSTRACT

A female incontinence device inserted into the vagina for supporting the vaginal tissue on each side of the upper urethra so that the tissue therebetween will be stretched like a hammock and will offer counter pressure to sudden increases in intra-abdominal pressure such as during coughing, sneezing, laughing and physical exercise thereby preserving continence. The device includes an annular inflatable body section having an aperture extending therethrough, means for inflating and deflating the body section and two projections attached to the body section for supporting the tissue of the vaginal wall lateral and adjacent to each side of the urethra therebetween. The inflating and deflating means includes a tubing extending from the body section, and a valve housed within the tubing for regulating the flow of air into and out of the body section.

7 Claims, 2 Drawing Sheets

FEMALE INCONTINENCE DEVICE

FIELD OF THE INVENTION

This invention relates to medical devices used in controlling urinary stress incontinence in women, and more particularly to a device inserted into the vagina for supporting the vaginal tissue on each side of the urethra so that the tissue therebetween is stretched during an increase in intra-abdominal pressure and can thereby offer counter pressure and preserve continence.

BACKGROUND OF THE INVENTION

Urinary incontinence in women is a common and potentially a serious social problem. Most often, the incontinence is of the stress type, i.e., it occurs when intra-abdominal pressure is suddenly raised as during coughing, sneezing, laughing and physical exercise. Sometimes the problem will only occur occasionally when intra-abdominal pressure is raised excessively. In other cases, a minimally exerted stress will cause leakage, particularly in the erect position. Repeated leakage may cause skin irritation and be an embarrassment to the patient, especially when it is noticeable as an offensive odor.

One solution to the problem of urinary incontinence is the use of absorbent pads in the genital region. However, these pads are unacceptable due to the limited volume of urine they can absorb, the associated odor, and the high probability that skin infection and inflammation will follow.

It has been proposed that urinary incontinence can be regulated by altering the angular relationship between the urethra and bladder. That is, it has been observed that by making the urethrovesical angle, i.e., the angle between the urethra and the bladder base, more acute, urinary incontinence can often be reduced. U.S. Pat. No. 3,705,575 to Edwards is based on this principle. It discloses an incontinence device that changes the urethrovesical angle. The device includes a first member which is adapted to fit within the vagina and which applies pressure to the urethra and a second member adapted to bear against the external pubic area of the female body. However, this device is uncomfortable to wear and may cause irritation to the vaginal mucosa. Furthermore, the device is not likely to stay in place when inserted into the vagina just inside the introitus and is not inflatable, and therefore, can not be expanded to give just the right amount of support.

Another incontinence device is that disclosed in U.S. Pat. No. 3,554,184 to Habib. The incontinence device is formed from silicon rubber and designed to be inserted into the external region of the vagina. The patient must wear a belt, coupled to the member, whereby the latter is thrust against the anterior wall of the vagina with a sufficient magnitude to efficiently block the flow of urine through the urethra. However, besides involving the wearing of an uncomfortable belt, the device is only partially contained within the vagina and may therefore cause irritation of the labia.

Bonner in U.S. Pat. No. 3,646,929 discloses a female incontinence device which comprises a generally flat support adapted for insertion into the vagina. A flexible diaphragm is coupled to the support and is inflated to expand in an upward direction against the anterior wall of the vagina for applying pressure thereupon to block the urethra. However, this device blocks all flow of urine from the bladder. Therefore, when a patient needs to urinate the device must be deflated and then inflated after micturition.

Corey in U.S. Pat. No. 4,139,006 discloses a device completely inserted into the vagina for displacing a surface of the anterior wall of the vagina, and an intermediate section of the urethra adjacent thereto, toward the pubic bone, thereby reducing the urethrovesical angle for restoring the patient's natural control of the flow of urine through the urethra from the bladder to the urethral opening. However this device is not likely to stay in place when inserted into the vagina only just inside the introitus, is not inflatable and, therefore, can not be expanded to give just the right amount of support.

Surgery offers another solution to the problem. Almost all surgical procedures improve support to the upper urethra which is thereby better exposed to changes in intra-abdominal pressure. When pressure is raised in the abdomen by a stress condition such as coughing, the increased pressure will be transmitted after the operation, not only to the bladder, but also to the same, or almost the same, extent to the upper urethra. Thus, a higher pressure in the upper urethra than in the bladder will be maintained regardless of pressure changes in the abdomen. Digital support on each side of the upper urethra, Bonney's maneuver, has often been tried by the physician examining prior to surgery. If such support inhibits incontinence caused by coughing it has been felt that the patient would be a good candidate for surgery. However, surgical procedures are often not to be considered due to the patient's age or medical status. Accordingly, a device for controlling urinary incontinence which overcomes the problems associated with the prior art devices disclosed herein, and which can be used temporarily until an operation can be carried out, or permanently if the patient is a poor operative risk, would be desirable. The device should permanently offer the same support as the examining physician's fingers are offering when Bonney's maneuver is carried out.

OBJECTS AND SUMMARY OF THE INVENTION

The primary object of the present invention is to provide an inflatable device which is completely inserted into the vagina and will control female stress incontinence, which device will prevent incontinence during stress conditions such as coughing, sneezing, laughing and physical exercise by improving transmission of intra-abdominal pressure to the upper urethra.

Another object of the present invention is to provide such a device which does not exert a permanent pressure over the urethra and therefore does not require removal or deflation to allow micturition.

Another object of the present invention is to provide such a device which exerts support on each side of the upper urethra.

Another object of the present invention is to provide such a device which is adjustable by inflation and thereby can be given a large volume and size when inserted but a reduced size during the actual insertion or removal.

Another object of the present invention is to provide such a device which is malleable so as to retain some shape and stiffness when not inflated.

Another object of the present invention is to provide an easily insertable device causing minimal discomfort and irritation to the patient.

Another object of the present invention is to provide a device of such a shape that it will grip to the walls of the vagina, thereby restricting the relative movement therebetween.

Another object of the present invention is to provide a device which is of such shape that it will allow vaginal drainage to migrate from the posterior section of the vagina to the introitus.

Another object of the present invention is to provide a device which will counteract prolapse of the uterus and vagina.

The device in accordance with the present invention does not primarily intend to affect the urethrovesical angle, nor exert a persisting pressure over the urethra, but it increases transmittance of intra-abdominal pressure to the upper urethra. By having such an effect, "closure pressure", defined herein as the greatest difference between intra-urethral and simultaneous bladder pressure, will remain positive regardless of the changes in the intra-abdominal pressure, and continence will be preserved.

The female incontinence device is inserted into the vagina for controlling female stress incontinence. The device includes an annular inflatable body section, means for inflating and deflating the body section and two projections attached to the body section for supporting the vaginal tissue on each side of the upper urethra so that the tissue between the projections of support will be stretched and can offer counter pressure when there is a sudden increase in intra-abdominal pressure. This will preserve continence since the urethra between the points of support will be more readily exposed to increases in abdominal pressure; closure pressure will remain positive.

The body section includes a roughened surface around the exterior portion thereof, capable of contacting the walls of the vagina to restrict the relative movement of the body section when positioned within the vagina. The body section also includes an aperture extending therethrough which reduces the total volume of the device, allows drainage of uterine secretions, and further restricts the relative movement of the body section when positioned within the vagina. The means for inflating and deflating the body section include a tubing extending from the body section, and a valve housed within the tubing or within the body section for regulating the flow of air into and out of the body section. For deflation of the device, the valve can be opened by digital compression carried out by an attendant or the patient herself.

The above will become more apparent to those skilled in the art after a consideration of the following detailed description taken in conjunction with the accompanying drawings in which a preferred form of this invention is illustrated.

DETAILED DESCRIPTION OF THE PREFERRED EMBODIMENT

The device in accordance with the present invention is used in controlling urinary incontinence in women. The device is completely inserted into the vagina for supporting the tissue of the vaginal wall on each side of the upper urethra so that, when the intra-abdominal pressure is suddenly increased, the vaginal tissue between the points of support will be stretched like a hammock and the tissue will offer counter pressure to the increasing intra-abdominal pressure. This will allow intra-abdominal pressure to be transmitted to the upper urethra so that the closure pressure, i.e., the greatest difference between intra-urethral and simultaneous bladder pressure, will remain positive regardless of the changes in the intra-abdominal pressure, and continence will be preserved. The support afforded to each side of the urethra allows the tissue between the points of support to function like a hammock such that the tissue will offer counter pressure to sudden increases in intra-abdominal pressure which occur during coughing, sneezing, laughing and physical exercise. Thus, the urethra will be totally affected by increases in intra-abdominal pressure and retain a pressure greater than in the bladder, such that the closure pressure will remain positive and continence will be preserved.

Figure 1:
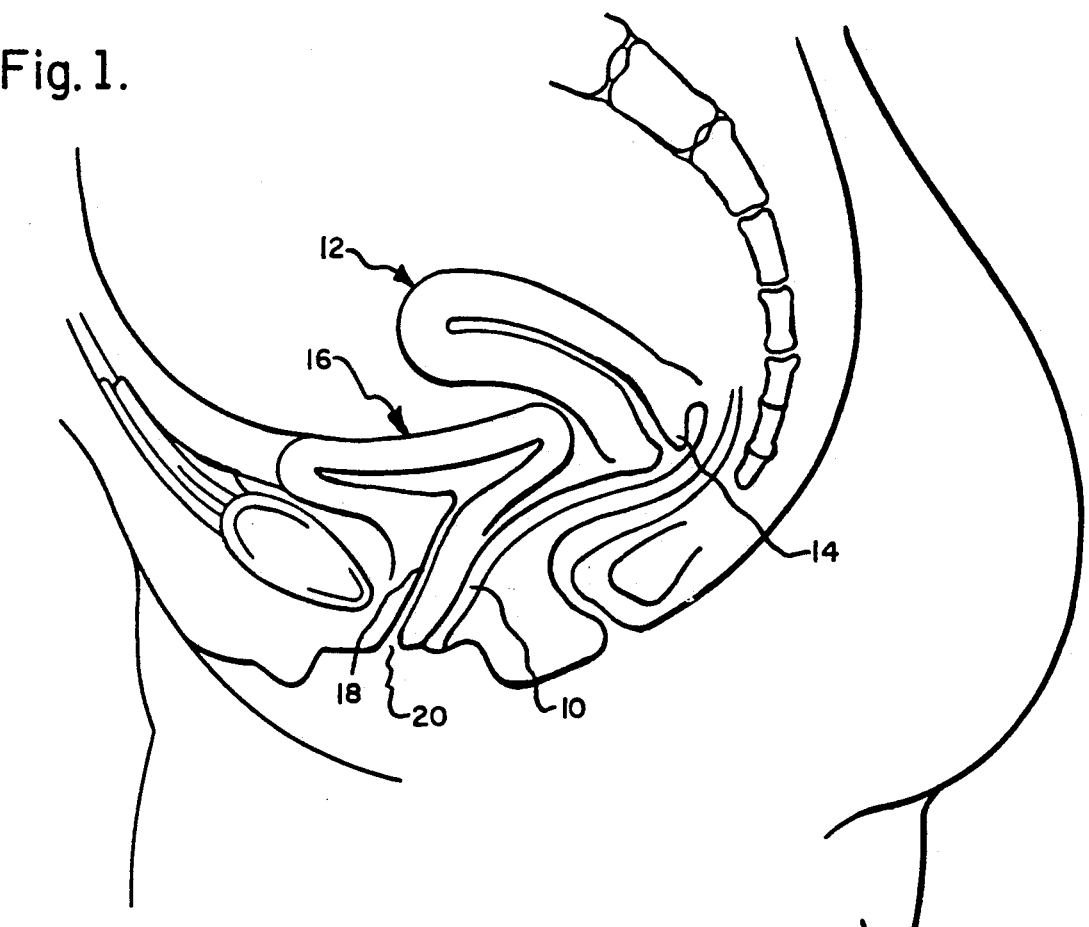
FIG. 1 illustrates a sagittal section of the female pelvis.

With reference to FIG. 1, there is shown a sagittal section of the female pelvic organs which contact the device of the present invention. The organs of interest include the vagina 10, the uterus 12, the cervix 14 at the lower end of the uterus 12 opening into vagina 10, the bladder 16 and urethra 18. Bladder 16 stores the urine and passes it through the urethra to the urethral opening 20 for discharge. When due to an activity such as coughing, sneezing, laughing or physical exercise, intra-abdominal pressure is suddenly raised, pressure in the bladder 16 is totally affected by this pressure increment. In women who suffer from stress incontinence the increased intra-abdominal pressure is only incompletely transmitted to the urethra and, at the peak of the stress situation, pressure is no longer higher in the urethra 18 than in the bladder 16, as it normally should be. Consequently there is nothing to prevent the urine from being extruded out through the urethral opening 20. The present device will correct this situation. It will improve transmittance of intra-abdominal pressure to the urethra which will thereby maintain a higher pressure than in the bladder regardless of changes in intra-abdominal pressure.

Figure 2:
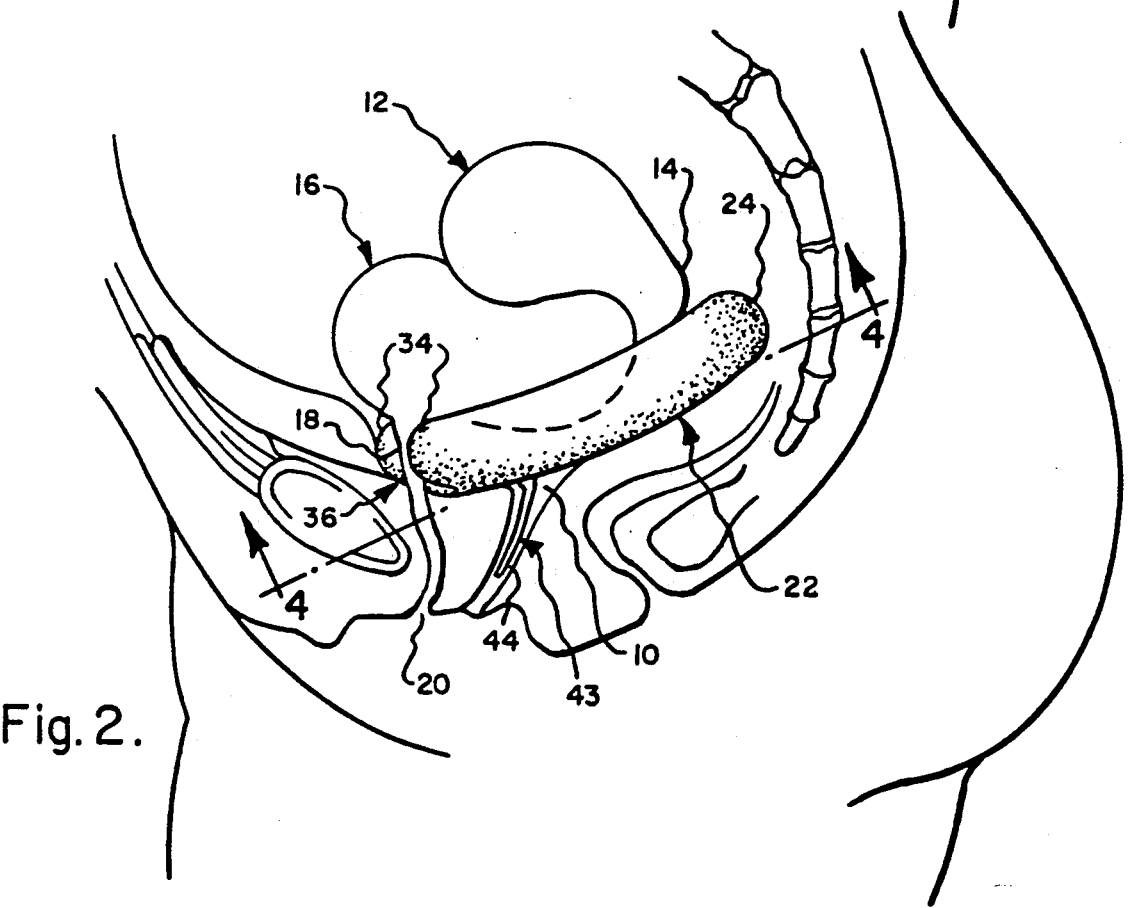
FIG. 2 is a view similar to FIG. 1 showing the device of the present invention within a vagina.
Figure 3:
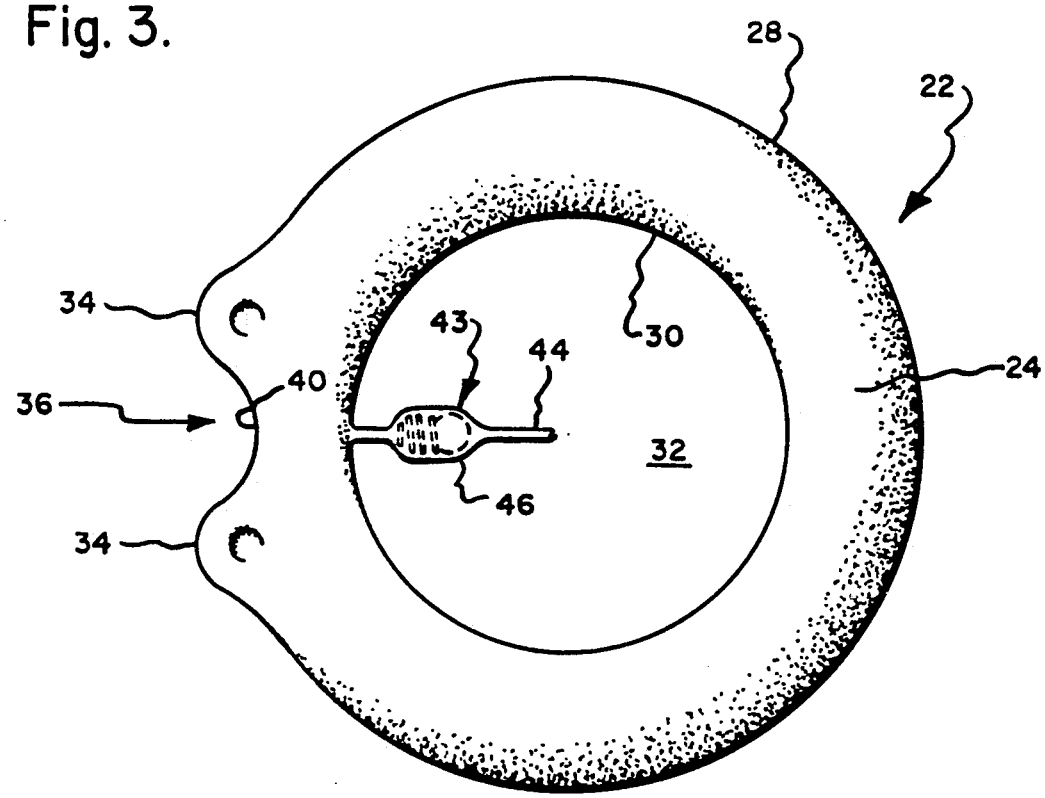
FIG. 3 illustrates a top view of the device of the present invention when inflated.
Figure 4:
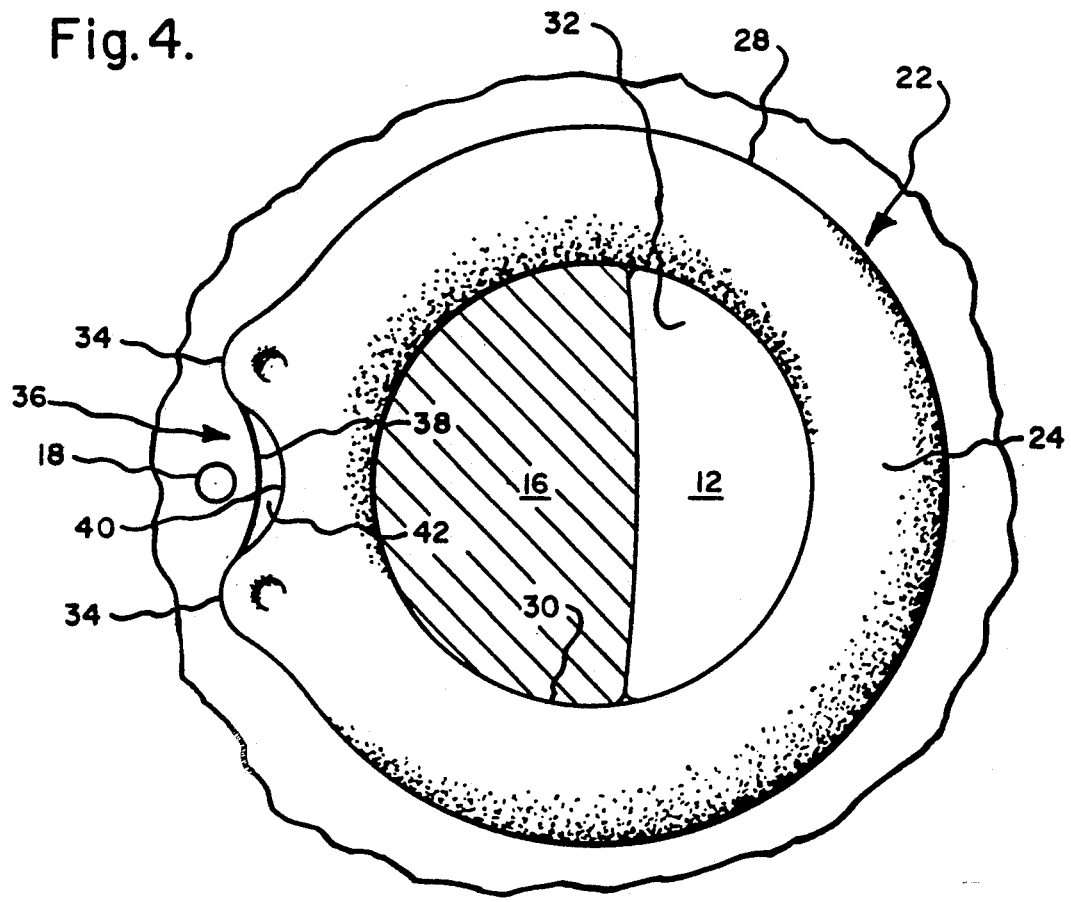
FIG. 4 is a view taken generally along the line 4—4 in FIG. 2.

With reference to FIGS. 2-4, the device of the present invention is indicated generally at 22 and includes a body section 24 having the form of a doughnut or ring. Body section 24 defines a roughened surface 28 on the axially exterior portion thereof and an axially inner surface 30. Surface 30 defines the outer diameter of an aperture 32 which extends through body section 24. The aperture 32 allows drainage to migrate from the uterus and out of vagina 10. A projection section, indicated generally at 36, is attached to and is formed as an integral part of body section 24 and includes two anterior projections 34 spaced along external surface 28 of body section 24. While the projections 34 described herein are formed integral to the body section 24, it is within the scope of the present invention to have projections which are separately attached to body section 24. The projections 34 provide support to the tissue of the anterior vaginal wall 38 (FIG. 4) on each side of the urethra 18 when device 22 is inserted in the vagina.

Projections 34 form a U-shaped surface 40 therebetween. This U-shaped surface is generally bisected by the major diameter of the body section 24 for providing a symmetrical force therealong. Projections 34, the contour of the U-shaped surface 40 and the overall dimensions of body section 24 are constructed to be comfortable and compatible with the anatomical structures of the female anatomy. The device 22 is molded as a smooth single unit composed of a pliable, resiliently deformable material such as an elastomer. The material should include characteristics which will readily deform when device 22 is folded for insertion within vagina 10 and during normal physical activity, but continually provide the required support to the tissue of the anterior vaginal wall 38 on each side of the urethra 18. When inserted, there is a void 42 between the tissue 38 of the anterior vaginal wall and the U-shaped surface 40, which void will permit the drainage of vaginal mucosa.

The device should be constructed of a material capable of expansion upon air inflation and contraction during deflation. With reference to FIG. 3, an inflation means, indicated generally at 43, is provided. The inflation means is operated by a syringe or a pump (not shown) and includes a tubing 44 connected to body section 24 at circumferential surface 30 and a one-way ball valve 46. Tubing 44 may extend outside the vagina for easy access. If so, it may be surrounded by a spiral spring (not shown) so it tends to stay within the vagina but can be pulled out for access. Alternatively, once device 22 has been inflated tubing 44, which originally is of considerable length to allow easy inflation, may be shortened by being cut off with scissors. For deflation, the valve 46 can be opened by digital compression carried out by an attendant or by the patient herself. It is understood, that any sufficient method of inflating and deflating body section 24 can be substituted herein and still be within the scope of the present invention.

The device 22 is inserted within vagina 10 so that projections 34 are on each side of the urethra 18 and exert no pressure on urethra 18. Projections 34 will offer support to the connective tissue of the anterior vaginal wall which is between the urethra and the vaginal mucosa. This tissue will act like a hammock and offer counter pressure to an increasing intra-abdominal pressure. Further, projections 34 enhance the natural gripping ability of the vaginal walls for retaining the device 22 in its proper location during most types of physical activity.

With reference to FIG. 2, the device 22 may be inserted into the vagina 10 in the doctor's office or by the patient at home. First, the doctor (or patient) grasps body section 24 of device 22 and squeezes the body section which will fold sagittally along the major diameter thereof. The device will then, when not inflated, have the shape of a section of a sphere. The concavity of the section should be facing the patient when she or the doctor introduces the device into the vagina until it reaches the posterior fornix. The insertion is similar to that of a diaphragm and is easier than the insertion of a stiff prolapse ring. As device 22 approaches the proper location, the doctor or patient then locates the two projections 34 and makes sure that they are on each side of the urethra and that the ring rests on the pubic arch and the levator muscles. Partially inflating device 22 through tubing 44 will facilitate positioning. When the correct position is secured device 22 is further inflated until it is noted that coughing no longer causes leakage. The diameter of device 22 may vary between 50 and 95 mm depending upon its original size and the degree of inflation.

The supporting pressure exerted against the vagina, laterally and adjacent to each side of the urethra, will allow the tissue 42 between the vaginal mucosa and the urethra 18 to function like a hammock, as shown in FIG. 4, and the tissue will offer counter pressure when intra-abdominal pressure is suddenly raised as it is during coughing, sneezing, laughing and physical exercise. Thus, the intra-abdominal pressure is transmitted to the upper urethra so that the closure pressure remains positive regardless of the changes in the intra-abdominal pressure such that continence is preserved.

The patient may proceed with normal physical activities characteristic of everyday life after device 22 is inserted within the vagina. Consequently, the patient may participate in physical activities which formerly would have been prohibited due to the danger of an unanticipated loss of urine responsive to the increased intra-abdominal pressure caused by the stress activities. The device may be worn continuously within the vagina of the patient without the removal thereof when the patient desires to urinate. For cleaning the device can be removed at the end of the day or, like other prolapse devices, it can be retained for up to one month.

It will be understood that the foregoing description and illustrations are by way of example only and that such modifications and changes as may suggest themselves to those skilled in the art are intended to fall within the scope of the present invention as defined by the appended claims.

What is claimed is:

1. A female incontinence device capable of being removably inserted into the vagina for supporting the tissue of the vaginal wall to each side of the urethra, comprising:

an annular inflatable body section for insertion into the vagina, the body section having an exterior surface capable of contacting the walls of the vagina when inflated so that relative movement of said body section with respect to the vagina is restricted, said body section including two projections, there being a U-shaped surface between the projections, the projections supporting the superior vaginal tissue on each side of the urethra in such a manner that the tissue therebetween is stretched and can offer counter pressure when intra-abdominal pressure is suddenly raised as occurs during coughing, sneezing, laughing and physical exercise such that the intra-abdominal pressure is transmitted to the upper urethra so that the greatest difference between intra-urethral and simultaneous bladder pressure remains positive regardless of the changes in the intra-abdominal pressure so continence is preserved; and means for inflating and deflating the body section so that proper support of the superior wall of the vagina is accomplished.

2. The female incontinence device of claim 1, wherein said exterior circumferential surface of said body section is roughened and contacts the walls of the vagina to restrict relative movement of said body section therebetween when positioned within the vagina.

3. The female incontinence device of claim 1, wherein said means for inflating and deflating said body section comprise a tubing attached to said body section and extending therefrom having a valve housed therein for regulating the flow of air into and out of said body section.

4. The female incontinence device of claim 3, wherein said valve is a one-way ball valve.

5. The female incontinence device of claim 4, wherein said one-way ball valve is opened by digital compression.

6. The female incontinence device of claim 1, wherein said projections are oriented generally parallel to the major diameter of said body section.

7. A method for controlling urinary incontinence in females comprising:

provilding an inflatable device having an annular inflatable body section capable of being removably inserted into the vagina, said body section having two projections extending therefrom for supporting the vaginal tissue on each side of the urethra so that the tissue therebetween is stretched and can offer counter pressure when intra-abdominal pressure is suddenly increased as it is during coughing, sneezing, laughing and physical exercise such that the intra-abdominal pressure is transmitted to the upper urethra so that the greatest difference between intra-urethral and simultaneous bladder pressure remains positive regardless of the changes in the intra-abdominal pressure so continence is preserved;

inserting said device into the vagina until it reaches the posterior fornix and said projections are positioned on each side of the urethra and said device is resting on the pubic arch and the levator muscles; and inflating said body section until sudden increases in intra-abdominal pressure no longer cause leakage of urine from the urethral opening.

* * * * *